US00PP23803P2

(12) United States Plant Patent
Klein

(10) Patent No.: US PP23,803 P2
(45) Date of Patent: Aug. 6, 2013

(54) ***VERONICA* PLANT NAMED 'CHARLOTTE'**

(50) Latin Name: *Veronica longifolia*
Varietal Denomination: Charlotte

(75) Inventor: Ruud Klein, Roelofarendsveen (NL)

(73) Assignee: Rijnbeek and Son Perennials-Export B.V., Boskoop (NL)

( * ) Notice: Subject to any disclaimer, the term of this patent is extended or adjusted under 35 U.S.C. 154(b) by 97 days.

(21) Appl. No.: 13/200,605

(22) Filed: Sep. 24, 2011

(51) Int. Cl.
*A01H 5/00* (2006.01)

(52) U.S. Cl.
USPC ..... Plt./251

(58) Field of Classification Search
USPC ..... Plt./251
See application file for complete search history.

*Primary Examiner* — Susan McCormick Ewoldt
(74) *Attorney, Agent, or Firm* — C. A. Whealy

(57) ABSTRACT

A new and distinct cultivar of *Veronica* plant named 'Charlotte', characterized by its upright plant habit; relatively small variegated leaves; dense inflorescences with numerous white-colored flowers; and good garden performance.

3 Drawing Sheets

Botanical designation: *Veronica longifolia.*
Cultivar denomination: 'CHARLOTTE'.

BACKGROUND OF THE INVENTION

The present invention relates to a new and distinct cultivar of *Veronica* plant, botanically known as *Veronica longifolia* and hereinafter referred to by the name 'Charlotte'.

The new *Veronica* plant is a naturally-occurring branch mutation of *Veronica longifolia* 'Melanie White', not patented. The new *Veronica* plant was discovered and selected by the Inventor on a single flowering plant from within a population of plants of 'Melanie White' in a controlled outdoor nursery environment in Roelofarendsveen, The Netherlands during the summer of 2007.

Asexual reproduction of the new *Veronica* plant by softwood cuttings in a controlled environment in Roelofarendsveen, The Netherlands since the summer of 2007, has shown that the unique features of this new *Veronica* plant are stable and reproduced true to type in successive generations.

SUMMARY OF THE INVENTION

Plants of the new *Veronica* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Charlotte'. These characteristics in combination distinguish 'Charlotte' as a new and distinct *Veronica* plant:

1. Upright plant habit.
2. Relatively small variegated leaves.
3. Dense inflorescences with numerous white-colored flowers.
4. Good garden performance.

Plants of the new *Veronica* differ primarily from plants of the parent, 'Melanie White', in the following characteristics:

1. Plants of the new *Veronica* have smaller leaves than plants of 'Melanie White'.

2. Plants of the new *Veronica* have variegated leaves whereas plants of 'Melanie White' have solid green-colored (non-variegated) leaves.

Plants of the new *Veronica* can be compared to plants of *Veronica longifolia* 'Schneeriesin', not patented. In side-by-side comparisons conducted in Roelofarendsveen, The Netherlands, plants of the new *Veronica* differed primarily from plants of 'Schneeriesin' in leaf color as plants of 'Schneeriesin' had solid green-colored (non-variegated) leaves.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of a typical flowering plant of 'Charlotte' grown in a container.

The photograph on the second sheet is a close-up view of a typical flowering plant of 'Charlotte'.

The photograph on the third sheet is a close-up view of a typical leaf of 'Charlotte'.

DETAILED BOTANICAL DESCRIPTION

Plants used for the aforementioned photographs and following description were grown during the summer in an outdoor nursery in Boskoop, The Netherlands and under environmental conditions and cultural practices which closely approximate commercial *Veronica* production. During the production of the plants, day temperatures ranged from 14° C. to 28° C. and night temperatures ranged from 8° C. to 16° C. Plants were one year old when the photographs and the description were taken. In the following description, color references are made to The Royal Horticultural Society Colour Chart, 2007 Edition, except where general terms of ordinary dictionary significance are used.

Botanical classification: *Veronica longifolia* 'Charlotte'.

Parentage: Naturally-occurring branch mutation of *Veronica longifolia* 'Melanie White', not patented.

Propagation:

*Type cutting*.—Softwood cuttings.

*Time to initiate roots*.—About three weeks at 22° C.

*Time to produce a rooted young plant*.—About six months at 14° C. to 28° C.

*Root description*.—Fine, somewhat fibrous; color, close to 199B to 199C.

*Rooting habit*.—Freely branching; medium density.

Plant description:

*Plant type*.—Herbaceous perennial.

*Plant and growth habit*.—Upright, narrow inverted triangle; basal branching habit with about four main stems; moderately vigorous growth habit; pinching will enhance lateral branch development.

*Plant height*.—About 41.6 cm.

*Plant width*.—About 20.1 cm.

*Lateral branch description*.—Length: About 25.5 cm. Diameter: About 3.5 mm. Internode length: About 3.5 cm. Strength: Strong. Texture: Densely pubescent. Color: Close to 144B; with development, color becomes closer to 144A with spots, close to 139A.

Foliage description:

*Arrangement*.—Opposite, simple.

*Length*.—About 5.5 cm.

*Width*.—About 2.5 cm.

*Shape*.—Ovate to narrowly ovate.

*Apex*.—Acute.

*Base*.—Short attenuate.

*Margin*.—Irregularly finely serrate.

*Texture, upper surface*.—Slightly rugose, sparsely pubescent.

*Texture, lower surface*.—Slightly rugose, pubescent.

*Venation pattern*.—Pinnate.

*Color*.—Developing leaves, upper and lower surfaces: Close to 146B; narrow margin, close to 150C to 150D. Fully expanded leaves, upper surface: Close to between 147B and 191A; narrow margin, close to between 150D and 157A; venation, close to 147C. Fully expanded leaves, lower surface: Close to 147B; narrow margin, close to between 150D and 157A; venation, close to 147C.

*Petiole length*.—About 1.3 cm.

*Petiole diameter*.—About 3 mm by 0.5 mm.

*Petiole texture, upper and lower surfaces*.—Smooth, glabrous.

*Petiole color, upper surface*.—Close to between 147B and 191A.

*Petiole color, lower surface*.—Close to 147B.

Flower description:

*Flower arrangement and shape*.—Single campanulate flowers arranged on compound terminal racemes; racemes dense; flowers face mostly outwardly.

*Flowering habit*.—Freely flowering, about 210 flowers per raceme.

*Fragrance*.—None detected.

*Natural flowering season*.—Plants begin flowering about eight months after planting; flowering continuous from late June to mid-August in The Netherlands.

*Flower longevity on the plant*.—About one week; flowers not persistent.

*Flower buds*.—Length: About 4.5 mm. Diameter: About 2.5 mm. Shape: Ovate. Color: Close to NN155D; calyx, close to 150D and 143A.

*Inflorescence height*.—About 10.6 cm.

*Inflorescence diameter*.—About 1.9 cm.

*Flower diameter*.—About 8 mm.

*Flower height*.—About 9 mm.

*Petals*.—Quantity and arrangement: About four in a single whorl, petals fused about 40% of the length from the base. Length: About 5 mm. Width: About 2.5 mm to 4.5 mm. Shape: Oblanceolate. Apex: Broadly acute. Margin: Entire. Texture, upper and lower surfaces: Smooth, glabrous. Color: When opening, upper and lower surfaces: Close to NN155D. Fully opened, upper and lower surfaces: Close to NN155D.

*Sepals*.—Quantity and arrangement: About four in a single whorl, sepals fused about 5% of the length from the base. Length: About 3 mm. Width: About 0.75 mm. Shape: Narrowly ovate. Apex: Acute. Margin: Entire. Texture, upper and lower surfaces: Smooth, glabrous. Color: When opening, upper and lower surfaces: Close to 150D and 143A, marbled. Fully opened, upper and lower surfaces: Close to 150D and 143A, marbled.

*Peduncles*.—Length: About 11.9 cm. Diameter: About 2 mm. Aspect: Primary racemes, mostly upright; secondary racemes, about 22.5° from vertical. Strength: Strong. Texture: Smooth, glabrous. Color: Close to 138A.

*Pedicels*.—Length: About 1.5 mm. Diameter: About 0.5 mm. Aspect: About 60° from peduncle axis. Strength: Strong. Texture: Smooth, glabrous. Color: Close to 138A.

*Reproductive organs*.—Stamens: Quantity per flower: Two. Filament length: About 6 mm. Filament color: Close to NN155D. Anther length: About 2 mm. Anther shape: Elliptical. Anther color: Close to 154C. Pollen amount: Scarce. Color: Greyed yellow. Pistils: Quantity per flower: One. Pistil length: About 8 mm. Stigma shape: Clavate. Stigma color: Close to 157D. Style length: About 7.5 mm. Style color: Close to NN155D. Ovary color: Close to 144B.

*Seeds and fruits*.—Seed and fruit development have not been observed on plants of the new *Veronica*.

Disease & pest resistance: Plants of the new *Veronica* have not been noted to be resistant to pathogens and pests common to *Veronica*.

Garden performance: Plants of the new *Veronica* have exhibited good garden performance and to tolerate rain, wind, high temperatures of about 35° C. and to be hardy to USDA Hardiness Zone 4.

It is claimed:

1. A new and distinct *Veronica* plant named 'Charlotte' as illustrated and described.

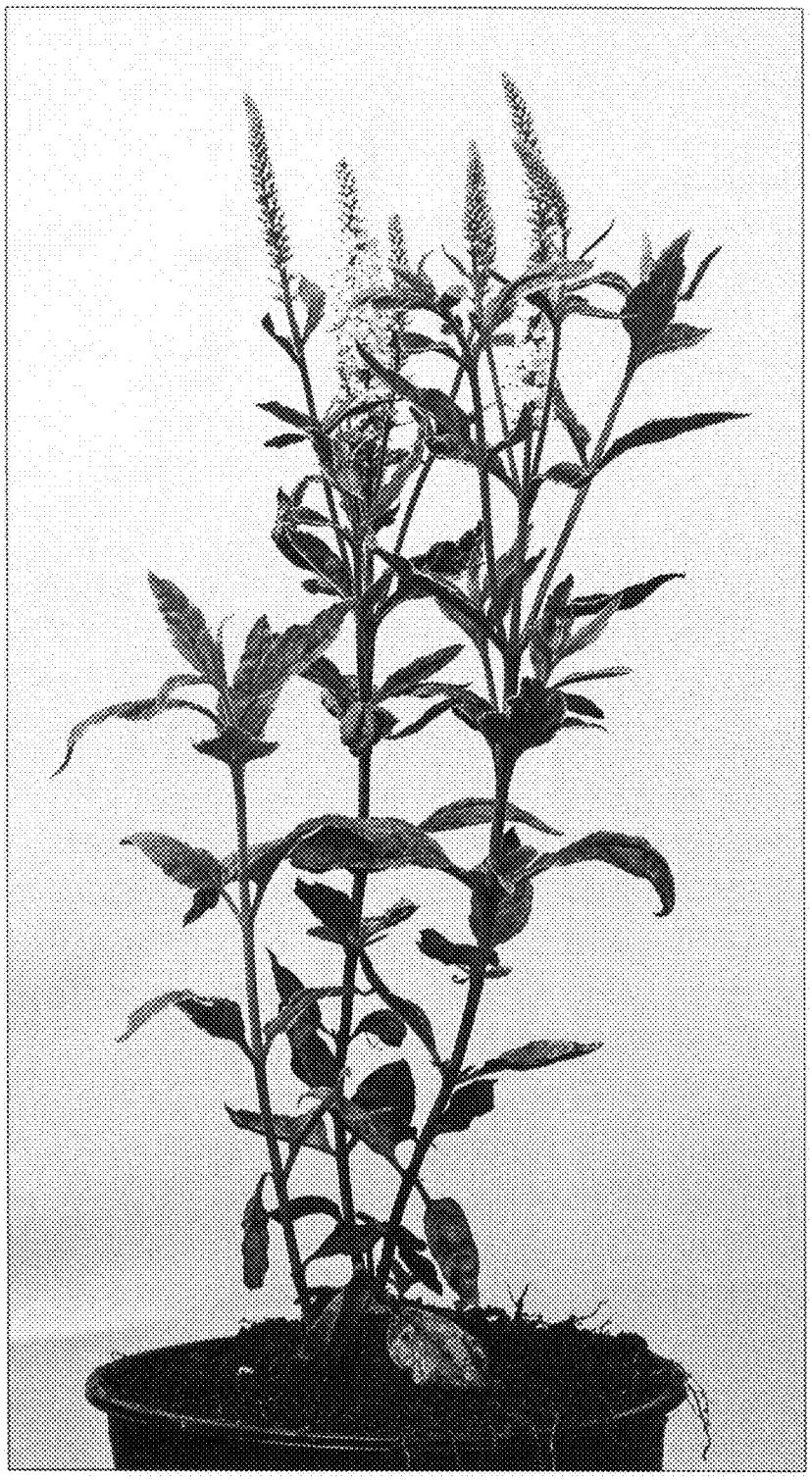

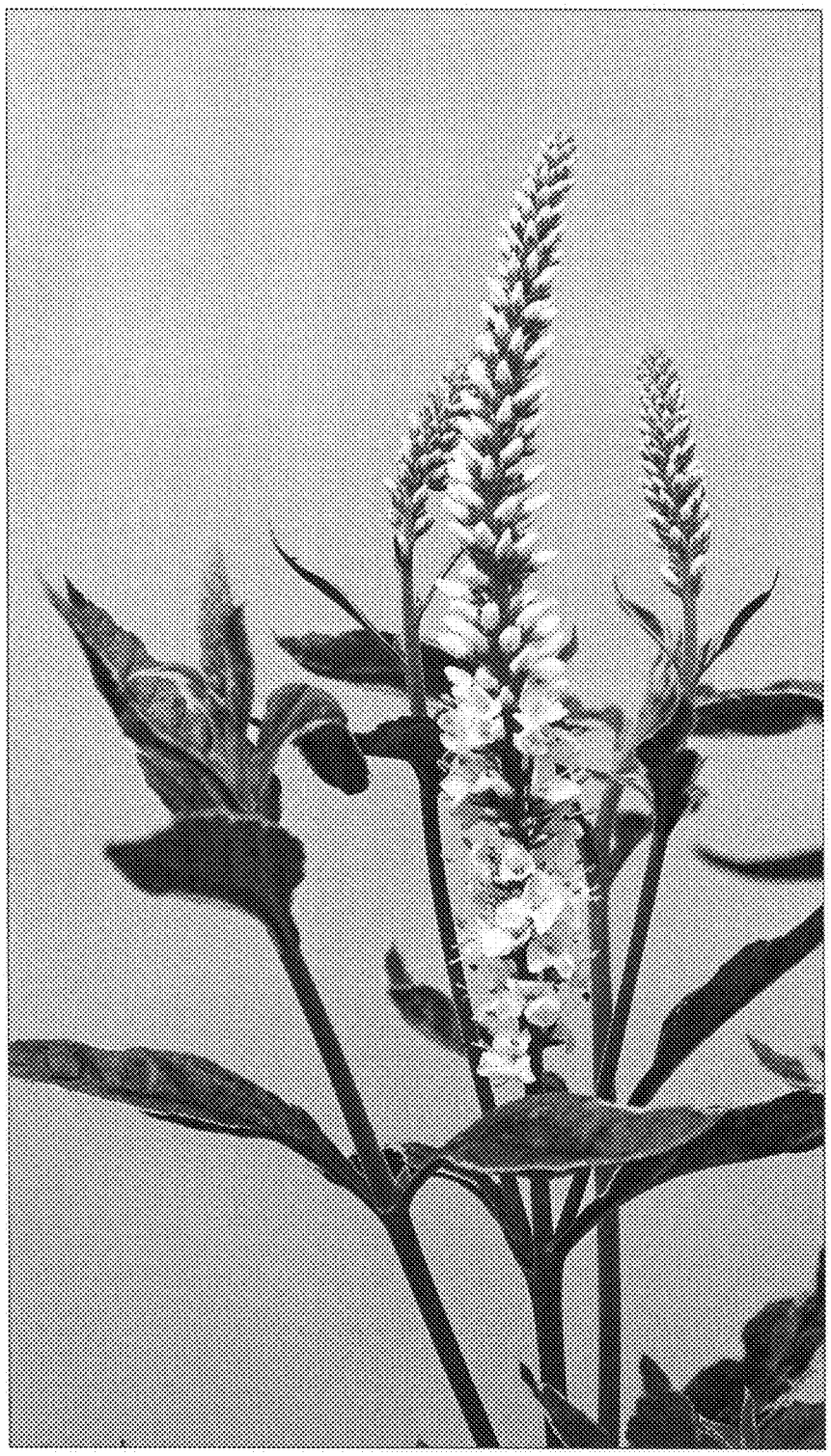

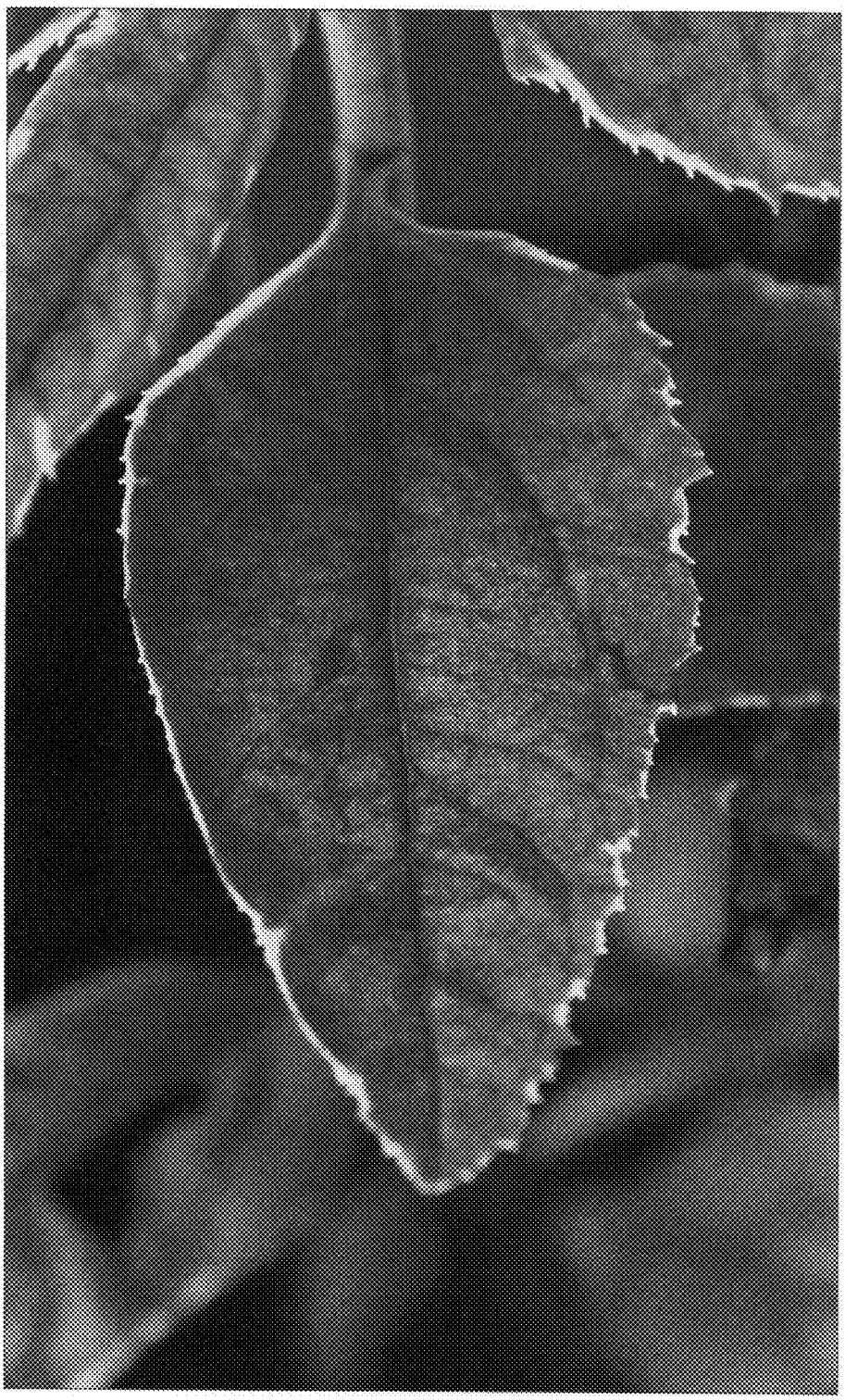

* * * * *